United States Patent [19]

Weissman

[11] Patent Number: 4,666,037
[45] Date of Patent: May 19, 1987

[54] DENTAL MODEL CARRIER

[76] Inventor: Bernard Weissman, 225 E. 48th St., New York, N.Y. 10017

[21] Appl. No.: 832,304

[22] Filed: Feb. 24, 1986

[51] Int. Cl.⁴ ............................................. B65D 81/02
[52] U.S. Cl. .................................... 206/63.5; 206/83; 206/470; 206/588
[58] Field of Search ................ 206/83, 461, 470, 63.5, 206/588; 433/25, 77, 79

[56] References Cited

U.S. PATENT DOCUMENTS

| | | | |
|---|---|---|---|
| 2,122,583 | 7/1938 | Parizot | 206/83 |
| 2,163,862 | 6/1939 | Wing | 206/83 |
| 2,196,566 | 4/1940 | Sabattis | 206/83 |
| 2,568,838 | 9/1951 | Wilcox | 206/83 |
| 2,620,919 | 12/1952 | Passmore | 206/83 |
| 2,973,767 | 3/1961 | Cohen | 206/83 |
| 4,101,031 | 7/1978 | Cromie | 206/588 |
| 4,236,637 | 12/1980 | Castner, Sr. et al. | 206/470 |
| 4,383,607 | 5/1983 | Lordahl et al. | 206/470 |

*Primary Examiner*—Joseph Man-Fu Moy
*Assistant Examiner*—Jimmy G. Foster
*Attorney, Agent, or Firm*—Goodman & Teitelbaum

[57] ABSTRACT

A protective carrier for a dental model which is used in the production of a dental prosthesis. The carrier includes three sections which are hinged together so that the sections can be folded over each other to close the carrier. A first section includes a centrally disposed tray section provided with a recessed cavity to receive a pedestal portion of the dental model. A second section includes a retaining sheet hinged to one side of the tray section, which can be folded onto the tray section and be slid between a locking position which secures the dental model in the cavity, and a release position permitting removal of the dental model from the cavity. A third section is a cover member which is hinged to an opposing side of the tray section and which closes onto the retaining sheet when folded on the tray section for protectively securing the dental model in the carrier. The cover member can also receive a die tray retaining the dental model therein.

22 Claims, 16 Drawing Figures

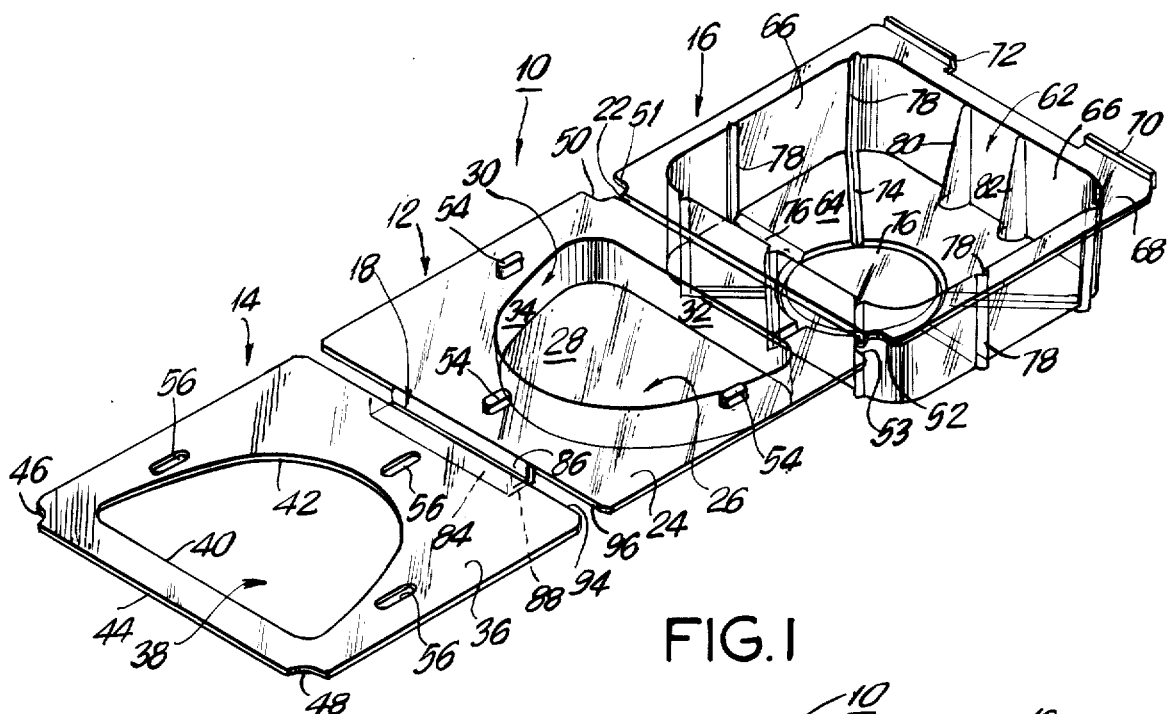

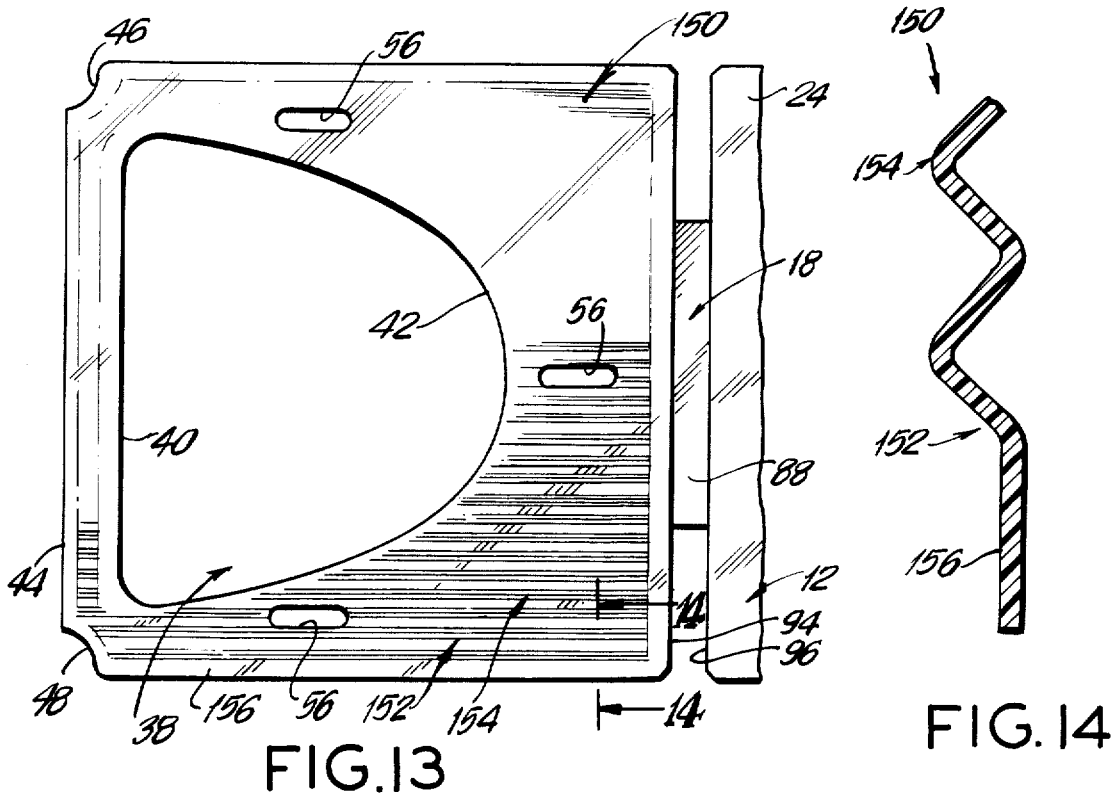
FIG.13
FIG.14
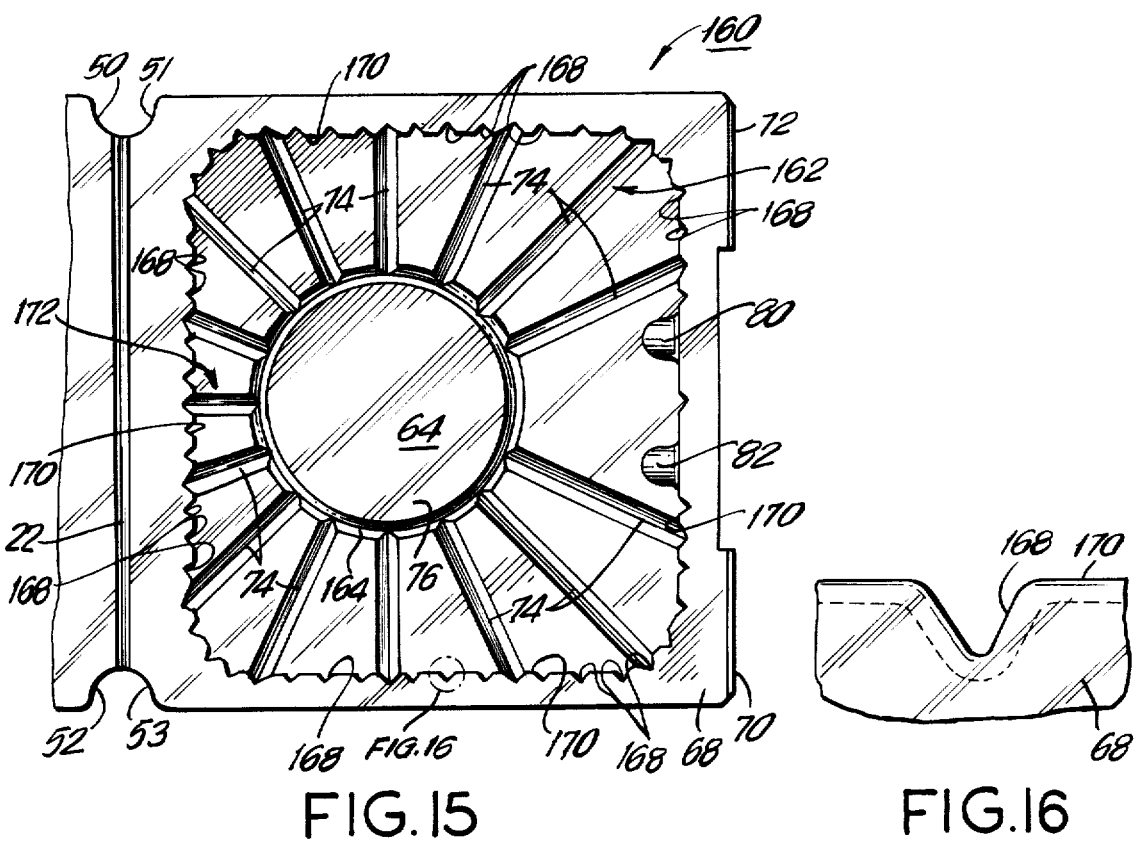
FIG.15
FIG.16

DENTAL MODEL CARRIER

BACKGROUND OF THE INVENTION

This invention relates to dental models, and more particularly to a protective carrier for retaining and transporting a dental model.

In various dental procedures, it is typical to form a dental model which is then used as a model base in the formation of a dental prosthesis. There are many steps needed in the production of such dental models. Typically, an imprint must be produced by the dentist in which the prepared teeth and gums are imprinted. The negative imprint is then filled by a special plaster mass at the laboratory or at the dentist's office. Positive models are then formed, hardened, and processed until a suitable dental model is produced. These steps not only require time and effort by the dentist and laboratory, but also require numerous visits of the patient to the dentist. It is therefore important that once a dental model is produced, it should be maintained in good condition without any cracking or chipping since any such damage to the dental model, usually formed of stone, would require a considerable amount of time, effort and cost to replace. Normally, once chipped or cracked, the dental model can no longer be utilized and must be entirely reconstructed.

The normal caution and care required for maintaining a dental model is made even more difficult since the dental model must frequently be manipulated by the dentist or laboratory. Furthermore, the dental model must be stored for considerable lengths of time and frequently must be transported between the dentist's office and the laboratory. Such lengthy storage and transport requirements also increase the possibility of damage or destruction of the dental model.

SUMMARY OF THE INVENTION

Accordingly, it is an object of the present invention to provide a dental model carrier which avoids the aforementioned problems.

Another object of the present invention is to provide a protective device for storing and transporting a dental model in a manner which prevents damage to the model.

A further object of the present invention is to provide a carrier for a dental model which permits the model to be carried either by itself or when the model is contained in a die tray.

Yet a further object of the present invention is to provide a dental model carrier which includes a cavity for receiving the dental model, the cavity preferably including a keyed seat for matingly receiving a correspondingly keyed pedestal portion of the dental model.

Still another object of the present invention is to provide a dental model carrier which can be used for protective transporting of the dental model, which also permits access to the dental model for further operations thereon.

Another object of the present invention is to provide a dental model carrier which includes a retaining sheet to hold the model in position within the carrier.

Briefly, in accordance with the present invention, there is provided a protective carrier for a dental model, the model being used in producing a dental prosthesis. The carrier includes a hinged three part interleaved arrangement. The first part includes a tray section having a recessed cavity for receiving the pedestal portion of the dental model. The second part includes a retaining sheet hinged to one side of the tray section, which is folded onto the tray section and serves to retain the dental mold in place in the cavity. The third part includes a cover member hinged to the opposite side of the tray section, which can close onto the retaining sheet and tray section for protectively securing the dental model in the carrier.

In an embodiment of the present invention, the retaining sheet is secured to the tray section by means of a flexible hinge. In this manner, in its folded position, the retaining sheet has limited sliding movement along the upper surface of the tray section. The retaining sheet can thereby move between a locking position, wherein a lip portion of the retaining sheet projects over the recessed cavity in the tray section, and a retracted position, wherein the lip portion is retracted from over the cavity. In the locked position, the lip portion can engage a ledge portion provided on the dental model to lock the dental model in place in the cavity. In its retracted position, the lip portion is removed from the cavity area to permit extraction of the dental model from the cavity.

A dental model is first seated in the cavity of the tray section. The retaining sheet is folded over onto the tray section and then slid to its locking position to lock the dental model in the cavity. The cover member is then folded onto the retaining sheet to permit storage and transport of the dental model.

In an embodiment of the present invention, a latch is provided at the edge of the cover member for engaging the edges of the retaining sheet and the tray section when the carrier is in its folded closed position. When latched, the latch serves to keep the retaining sheet in its locking position to hold the dental model in the cavity. The cavity in the tray section can be appropriately keyed in order to receive a mating keyed pedestal portion of the dental model.

A recessed chamber can be formed into the cover member for closing onto the folded retaining sheet so that the chamber is in communication with the cavity through an opening in the retaining sheet. The chamber can accommodate the upwardly projecting teeth of the dental model when the dental model is held in the cavity. A pair of spaced apart ribs can also be provided along a peripheral wall of the recessed chamber to accommodate mating tabs of a dental die tray. In this manner, if the dental model is maintained in a die tray, the die tray can be securely retained in the recessed chamber in the cover member with the projecting teeth of the dental model now being received in the cavity of the tray section.

BRIEF DESCRIPTION OF THE DRAWINGS

With the above and additional objects and advantages in view, as will hereinafter appear, this invention comprises the devices, combinations, and arrangements of parts hereinafter described by way of example, and illustrated in the accompanying drawings of a preferred embodiment in which:

FIG. 1 is a perspective view of the dental model carrier in its open position, showing the three part hinged arrangement including a retaining sheet, a tray section, and a cover member;

FIG. 2 is a top view of the open dental model carrier shown in FIG. 1;

FIG. 3 is a side elevational view of the open dental model carrier shown in FIG. 1;

FIG. 4 is a fragmented enlarged cross sectional view taken along line 4—4 of FIG. 3 through a projecting guide dimple which cooperates in the sliding of the retaining sheet along the tray section;

FIG. 5 is a side elevational view of the dental model carrier in its closed position;

FIG. 13 is a fragmented top view of an alternate embodiment of the retaining sheet, the retaining sheet being formed of corrugated material for improved stiffness;

FIG. 14 is a fragmented enlarged cross sectional view through a portion of the corrugations shown in FIG. 13, being taken along line 14—14 of FIG. 13;

FIG. 15 is a fragmented top view of an alternate embodiment of the cover member, showing the presence of additional radial stiffening ribs with corrugations being formed about the peripheral wall of the chamber for improved stiffness; and FIG. 16 is a fragmented enlarged view showing one of the corrugations formed into the peripheral wall about the chamber, being taken at area 16 of FIG. 15.

In the various figures of the drawings, like reference characters designate like parts.

DESCRIPTION OF THE PREFERRED EMBODIMENTS

Figure 6:
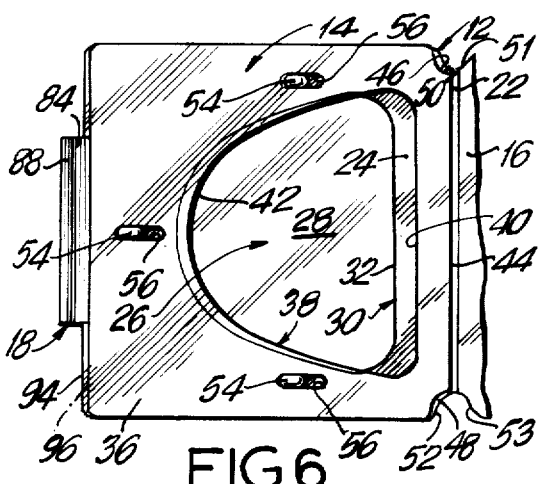
FIG. 6 is a fragmented top view of the carrier, showing the retaining sheet folded over the tray section, the retaining sheet being in its locking position.

Referring now to FIGS. 1-5, there is shown a dental model carrier 10 having three sections including a centrally positioned tray section 12, a laterally positioned retaining sheet 14, and an opposing laterally positioned cover member 16. A U-shaped flexible hinge 18 interconnects the sheet member 14 to one side of the tray section 12. Another flexible hinge 22 interconnects the cover member 16 to the opposite side of the tray section 12. The entire carrier 10 can be integrally formed of a unitary one-piece construction, and can be formed of transparent plastic material, or the like.

The tray section 12 includes an upper planar top wall 24 of substantially rectangular configuration. A D-shaped cavity 26 is recessed beneath the top wall 24 and includes a base wall 28 and peripheral side wall 30. The side wall 30 includes a straight wall side 32 adjacent the hinge 22, and an arcuate wall section 34.

The retaining sheet 14 is formed of a planar sheet member 36 having a cut out therefrom to provide an aperture 38 which, with the sheet member 36 folded onto the top wall 24, will correspond in shape substantially to the arcuate shape of the cavity 26. The aperture 38 includes a straight edge 40 and an arcuate edge 42. The distal end 44 of the sheet member 36 includes notched corners 46, 48 to matingly overlie the notched corner sections 50, 52 of the top wall 24 at opposing ends of the hinge 22 when the sheet member 36 overlies the tray section 12. Accordingly, the top wall of the cover member 16 also includes notched corner sections 51, 53 at the opposing ends of the hinge 22 to overlie the notched corners 46, 48 and the notched corner sections 50, 52 in the folded closed position of the carrier 10.

Upwardly projecting from the top wall of the tray section 12 are shown three oval projections 54. Corresponding to these projections 54 are provided three elongated slots 56 in the retaining sheet member 36. As will hereinafter be explained, the projections 54 are received in the elongated slots 56 and can slide therein. As best shown in FIG. 4, the projections 54 can be upwardly formed from the top wall 24 of the tray section 12 and can have a substantially rectangular cross sectional configuration. For aiding in retaining the slots 56 onto the projections 54 can have a narrower neck portion 58 which is slightly inwardly tapered from the upper end 60, so as to permit the slot to snap fit over the larger upper end 60 thereof.

The cover member 16 includes a recessed chamber 62 including a base wall 64 and peripheral side walls 66 to form a substantially rectangular configuration. A top wall 68 extends outwardly from the upper edges of the side walls 66. At the distal free end of the top wall 68, there are formed upwardly projecting tabs 70, 72 which are slightly inwardly curved so as to form a latch to lock the cover member 16 over the tray section 12 when the retaining sheet 14 is folded onto the tray section 12. The tabs 70, 72 latch over the edges of the top wall 24 of the tray section 12 and the sheet member 36 of the retaining sheet 14, as shown in FIG. 5.

A plurality of ribs 74 are formed radially along the surface of the base wall 64 of the chamber 62, projecting from an upwardly extending ribbed boss surface 76 for stiffening the cover member 16. The radial ribs 74 can also extend into vertical ribs 70 which project from the peripheral side walls 66 to provide additional stiffening of the side walls 66.

At the forward peripheral wall 66, adjacent the tabs 70, 72, there are provided two spaced apart posts 80, 82 which are upwardly tapered. These posts 80, 82 are available for retaining a die tray in the chamber 62, as will hereinafter be explained.

As is best seen in FIG. 2, the peripheral planar configuration of all three sections 12, 14, 16 of the dental model carrier 10 are substantially similar in size. In this manner, the retaining sheet 14 can easily fold onto the tray section 12, and the cover member 16 can fold onto the two other folded together sections 12, 14 to form a composite carrier 10 having a substantially uniform peripheral edge. Once assembled, as shown in FIG. 5, the protective carrier 10 will be retained by the tabs 70, 72 in a locked position, and thus serves to hold a dental model inserted therein.

It should be appreciated, that the hinge 18 only extends partway between the retaining sheet 14 and the tray section 12, being specifically in the mid-section thereof. As a result, with the retaining sheet 14 folded onto the tray section 12, the medial edges on either side of the hinge 18 will be available for receiving the corresponding latch tabs 70, 72 of the cover member 16.

Figure 7:
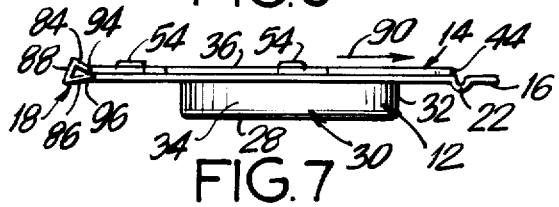
FIG. 7 is a fragmented side elevational view of FIG. 6, indicating the sliding action for placing the retaining sheet into its locking position.

Referring now to FIGS. 6-9, it will be noted that when the retaining sheet 14 is folded onto the tray section 12, the elongated slots 56 snap onto the projections 54. The retaining sheet 14 will therefore be maintained in surface contact with the upper surface of the top wall 24 of the tray section 12. The flexible hinge 18 includes a pair of opposing legs 84, 86 with an interconnecting bight portion 88. Being flexible, the opposing legs 84, 86 can laterally shift with respect to each other. In this manner, as shown in FIG. 7, with the projections 54 engaged within the slot 56, the retaining sheet 14 can be slid to the right, as shown by arrow 90, to move the U-shaped hinge 18 onto a first configuration which is angled towards the right.

In so doing, the aperture 38 formed in the retaining sheet 14 becomes offset with respect to the cavity 26 in the tray section 12. Since both the cavity 26 and the aperture 38 are of substantial identical planar shape, when in the offset configuration, the arcuate wall 42 of the aperture 38 forms a lip 91 which overhangs a portion of the cavity 26. Typically, a dental mold would be formed with a pedestal portion with teeth upwardly projecting from the pedestal. However, an inwardly directed flange or ledge is formed between the pedestal portion and the teeth. The projecting lip 91 overlying the cavity 26 will engage that ledge of the dental model so as to secure the dental model in place in the cavity 26.

Figure 9:
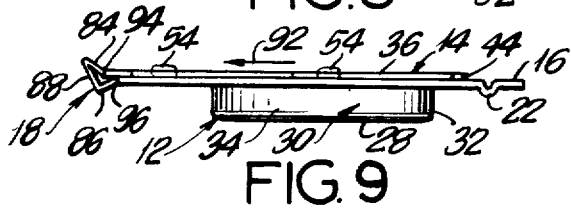
FIG. 9 is a fragmented side elevational view of FIG. 8, indicating the sliding action for placing the retaining sheet into its retracted position.

When it is desired to remove the dental model from cavity 26, the retaining sheet 14 is slid back in the direction shown by the arrow 92 in FIG. 9, so as to align the aperture 38 with the cavity 26. The projections 54 will slide within the slot 56 during this movement. In so doing, the hinge 18 is now moved into a second configuration which is angled towards the left, with the legs 84, 86 shifting in opposing directions.

Figure 8:
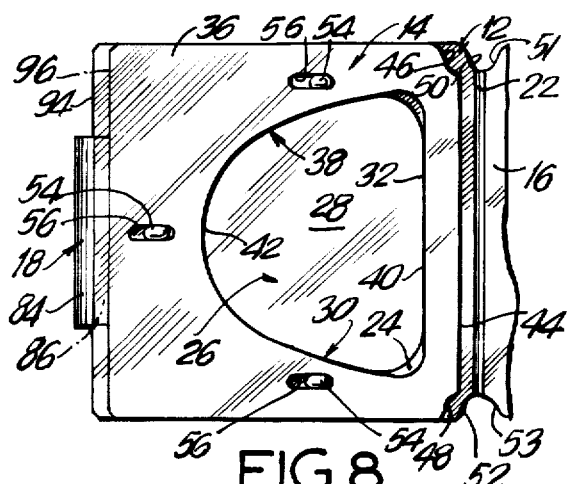
FIG. 8 is a fragmented top view similar to that shown in FIG. 6, showing the retaining sheet in its retracted position.

As noted by comparing FIG. 6 with FIG. 8, when the retaining sheet 14 is shifted into its locking position, as indicated in FIG. 6, the medial edge 94 of the retaining sheet 14 and the medial edge 96 of the tray section 24 are substantially aligned with each other. On the other hand, when the retaining sheet 14 is shifted to its retracted or unlocked position, as shown in FIG. 8, the medial edge 94 of the retaining sheet 14 extends leftward from the medial edge 96 of the tray section 12. It should therefore be appreciated that when the cover member 16 folds on top of the retaining sheet 14, since the tabs 70, 72 must snap onto the medial edges 94, 96 on either side of the hinge 18, the latching of the cover member 16 serves to align the edges 94, 96 as indicated in FIGS. 5-7, thereby forcing the retaining sheet 14 into its locking position. In this manner, the carrier 10 inherently serves to lock the dental model in place when in its closed position to thereby prevent the model from shifting around and moving within the dental carrier 10.

Figure 10:
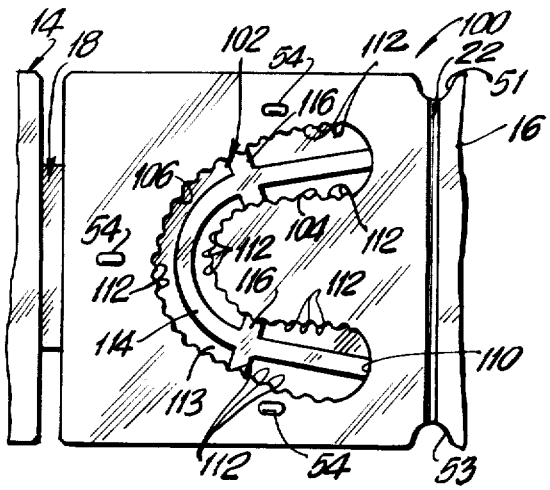
FIG. 10 is a fragmented top view of the tray section of the carrier tray, showing the cavity therein being provided with a keyed arrangement in order to receive a mating keyed pedestal portion of a dental model.

Referring now to FIG. 10, there is disclosed another embodiment of the tray section, showing a tray section 100 having a differently shaped cavity 102. The cavity 102 is specifically designed to accommodate a keyed pedestal portion of a dental model. The particular keyed arrangement shown is one that will accommodate a dental model described in U.S. Pat. No. 4,538,987 granted to the Applicant. In such patent there is described a dental model which includes a keyed arrangement formed of a plurality of corrugations, teeth or ribs, which are cast directly into the pedestal portion of the dental model, as described below with respect to FIG. 11. There is also provided an arcuate rib cast into the bottom surface of the model. The keyed arrangement described in the aforementioned patent is directed to a particular dental die tray which also includes a mating keyed arrangement for receiving the dental model.

Cavity 102 formed in the tray section 100 is of substantially U-shaped configuration having inner and outer walls 104, 106 interconnected by rounded end walls 108, 110. The arcuate inner and outer walls 104, 106 include corrugations or teeth 112 which protrude into the cavity 102. The corrugations 112 are uniform in projection, but certain of these can be wider than others. The cavity 102 can typically widen as it progresses from a lower to an upper edge thereof, in order to form an outwardly flared cavity to better receive the dental model. At the bottom 113 of the cavity 102, and projecting upwardly into the cavity 102, is an arcuate rib 114 including a plurality of laterally extending reinforcing webs 116.

Figure 11:
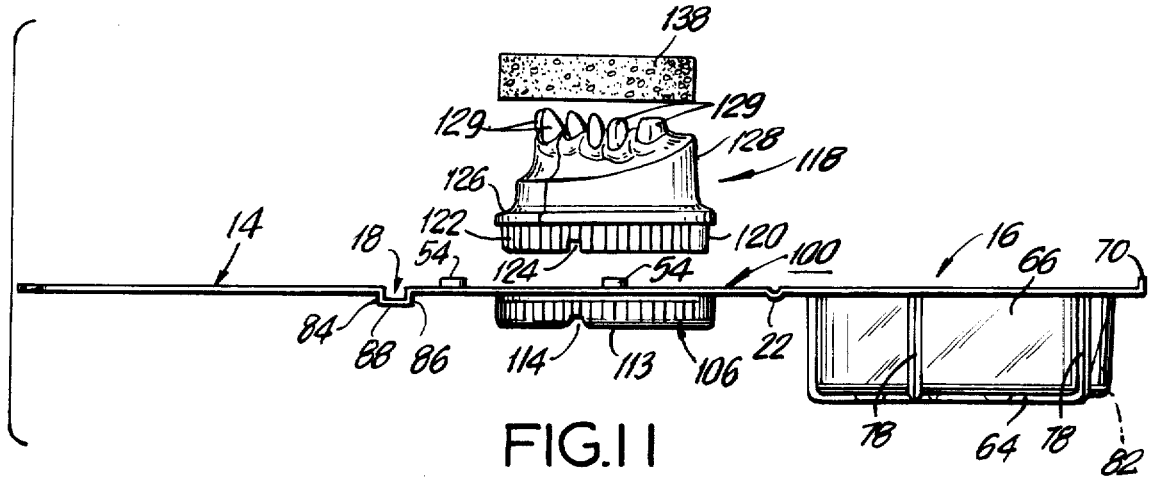
FIG. 11 is a side elevational view of an opened carrier tray having the tray section of FIG. 10, showing the receiving of a dental model into the carrier with the dental model having a keyed pedestal portion.

As shown in FIG. 11, the particular dental model described in the heretofore described patent, is shown generally at 118 and includes a base pedestal portion 120 on which is formed the peripheral keyed arrangement 122 and including an embededded groove 124 to accommodate the rib 114. A ledge 126 is typically formed on top of the pedestal portion 120. Upwardly projecting from the ledge 126, is the upper portion 128 of the dental model having the teeth 129 thereon.

The particular dental model 118 is inserted into the tray section 100 having the keyed arcuate cavity 102 formed therein. The keyed arrangement 122 of the pedestal portion 120 of the dental model 118 mates with the corrugations 112 of the cavity 102 provided therefor. Once inserted, the retaining sheet 14 is folded onto the dental model 118. The projections 54 fit within corresponding slots 56 provided within the retaining sheet 14 to aid in the sliding of the retaining sheet 14 into a locking position to lock the dental model 118 within the cavity 102. The cover member 16 is then closed onto the folded sections 14, 100, and locked in place by means of the latch tabs 70, 72. Typically, a foam spacer 138 is placed on top of the teeth 129 in order to accommodate any spacing between the teeth 129 and the inner surface of the cover member 16.

Figure 12:
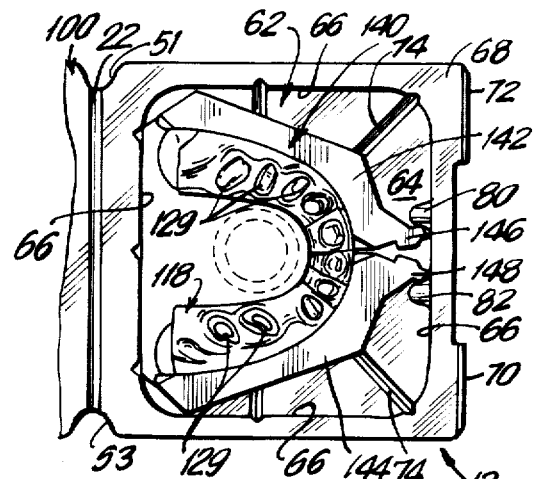
FIG. 12 is a fragmented top view of the cover member of the carrier, showing the retention therein of a dental die tray.

As shown in FIG. 12, the cover member 16 can receive the dental tray heretofore described in the aforementioned patent. In that patent, there is described a dental die tray including a pair of retaining arms abutting the die tray. The die tray is utilized to securely hold a dental model during the course of its production. Once the dental model is inserted in the die tray, it may be desirable to transport the dental model in the die tray. The particular die tray is shown generally at 140 in FIG. 12, and includes the opposing arms 142, 144 which are pivotally connected to the die tray 140 to retain the dental mold 118 secured in the die tray 140. At the ends of the pivotal arms 142, 144, there are provided a pair of handles 146, 148 which snap together to lock the arms 142, 144 in place. The ribs 80, 82 projecting from the chamber bottom wall 64 of the cover member 16 are spaced apart so as to accommodate the locking handles 146, 148 of the dental die tray 140.

With the dental model 118, which has been cut into sections, being retained in the dental die tray 140, where the arms 142, 144 hold the sections in place, the die tray can be inserted in the cover member 16, as shown in FIG. 12, where the teeth 129 will project upwardly from the cover member 16. In this case, the teeth 129 will be received through the aperture 38 of the retaining sheet 14 and into the cavity 102 of the tray section 100 or into the cavity 26 of the tray section 12. Thus, the carrier can be reversed, and the chamber 62 can alternatively serve as the compartment for receiving the dental model when disposed in the die tray, and the tray section with the retaining sheet folded thereon can be folded over the dental model and die tray, where the model teeth would project upwardly through the aperture in the retaining sheet into the cavity provided in the tray section.

It should therefore be appreciated, that by means of the present carrier, the dental model can be carried by itself, by inserting it into the cavity of the retaining section and using the cover member on top of the retaining member so that the model teeth project upwardly from the cavity into the cover chamber. Alternately, the cover member can be used as the receiving member when the dental model is retained in a dental die tray, and the tray section can be utilized as the cover thereto, so that the model teeth project upwardly into the cavity of the tray section.

In order to provide additional stiffening and reinforcement to the carrier structure, the retaining sheet can be formed of corrugated material, as shown in FIGS. 13 and 14. Specifically, a retaining sheet 150 is shown to include an arrangement 152 of a plurality of corrugation throughout its surface 154. However, preferably, a peripheral flat border 156, shown enlarged in FIG. 14, is formed about the edge thereof to permit the cover member 16 to lie flat onto the surface of the retaining sheet 150.

Additional support can also be provided to the cover member, as shown in FIGS. 15 and 16. Cover member 160 is shown to include an arrangement 162 of a plurality of extra ribs 74 radially extending from the circular rib 164 around the center boss area 76. Additionally, a plurality of corrugations or teeth 168 are formed in the peripheral wall 170 disposed about the chamber 172 in the cover member 160. The corrugations 168 are shown enlarged in FIG. 16, and provide for additional reinforcement.

There has been disclosed heretofore the best embodiment of the invention presently contemplated. However, it is to be understood that the present disclosure relates to a preferred embodiment of the invention which is for purposes of description only and is not to be construed as a limitation of the invention.

What is claimed is:

1. A protective carrier for a dental model used in producing a dental prosthesis, said carrier comprising:
   three interleaved sections;
   a first of said sections including a tray section provided with a recessed cavity for receiving a pedestal portion of a dental model;
   a second of said sections including a retaining sheet disposable onto said tray section, said retaining sheet including engagement means for holding the dental model in said cavity;
   a third of said sections including a cover member for closing onto said retaining sheet to protectively secure the dental model in said carrier when said carrier is in a closed position with said retaining sheet disposed between said tray section and said cover member; and
   flexible hinge means for pivotally interconnecting said retaining sheet to said tray section, said flexible hinge means permitting surface sliding of said retaining sheet along said tray section between a locking position for holding the dental model in said cavity and a retracted position for permitting removal of the dental model from said cavity.

2. A protective carrier as in claim 1, wherein said carrier has an integral one piece construction, said flexible hinge means pivotally connecting said retaining sheet to one side of said tray section, and second hinge means pivotally connecting said cover member to an opposing side of said tray section.

3. A protective carrier as in claim 1, wherein said engagement means includes a lip portion on said retaining sheet which projects over said recessed cavity when said retaining sheet is in said locking position to engage a ledge provided on the dental model, and which retracts from said recessed cavity when said retaining sheet is in said retracted position to release the dental model.

4. A protective carrier as in claim 1, wherein said tray section is provided with a plurality of projections extending from an upper surface of said tray section, mating elongated slots being provided in said retaining sheet for respectively receiving therein said projections in a folded-over position of said retaining sheet on said tray section, said projections sliding in their respective slots as said retaining sheet slides along said tray section between said locking position and said retracted position.

5. A protective carrier as in claim 1, wherein latch means are provided on said cover member for latching onto edges of said retaining sheet and said tray section in said closed position, said latch means maintaining said retaining sheet in said locking position when said latch means are latched.

6. A protective carrier as in claim 5, wherein said flexible hinge means extend along medial edge portions between said retaining sheet and said tray section, and said latch means being provided along opposite outer edge portions of said cover member to latch on opposite sides of said flexible hinge means.

7. A protective carrier as in claim 1, wherein said flexible hinge means includes an integral U-shaped hinge member having opposing legs interconnected by a bight portion, said legs being shiftable with respect to each other.

8. A protective carrier for a dental model used in producing a dental prosthesis, said carrier comprising:
   three interleaved sections;
   a first of said sections including a tray section provided with a recessed cavity for receiving a pedestal portion of a dental model;
   a second of said sections including a retaining sheet disposable onto said tray section, said retaining sheet including engagement means for holding the dental model in said cavity;
   a third of said sections including a cover member for closing onto said retaining sheet to protectively secure the dental model in said carrier when said carrier is in a closed position with said retaining sheet disposed between said tray section and said cover member;
   an aperture being provided in said retaining sheet; and
   an edge of said aperture defining said engagement means which projects over said recessed cavity to engage a ledge provided on the dental model.

9. A protective carrier as in claim 8, wherein said carrier has an integral one piece construction, first hinge means pivotally connecting said retaining sheet to one side of said tray section, and second hinge means pivotally connecting said cover member to an opposing side of said tray section.

10. A protective carrier as in claim 8, wherein said aperture corresponds in shape to a planar configuration of said cavity.

11. A protective carrier as in claim 10, wherein said cavity and said aperture are substantially D-shaped in cross section, and wherein the aperture shape mates with the cavity shape when said retaining sheet overlies said tray section.

12. A protective carrier as in claim 10, wherein said cavity includes U-shaped walls and said aperture includes U-shaped edges, and wherein said aperture edges mate with said cavity walls when said retaining sheet overlies said tray section.

13. A protective carrier as in claim 12, wherein said cavity includes a continuous peripheral arcuate side wall structure including facing outer and inner U-shaped cavity walls interconnected by rounded end walls, continuous teeth being disposed on said facing cavity walls, said teeth extending into said cavity.

14. A protective carrier for a dental model used in producing a dental prosthesis, said carrier comprising:
    three interleaved sections;
    a first of said sections including a tray section provided with a recessed cavity for receiving a pedestal portion of a dental model;
    second of said sections including a retaining sheet disposable onto said tray section, said retaining sheet including engagement means for holding the dental model in said cavity;
    a third of said sections including a cover member for closing onto said retaining sheet to protectively secure the dental model in said carrier when said carrier is in a closed position with said retaining sheet disposed between said tray section and said cover member;
    said cover member including a recessed chamber for overlying the dental model retained in said cavity;
    said chamber including a peripheral wall; and
    a pair of spaced posts being provided on said peripheral wall for retaining a dental die tray inserted within said chamber, the die tray holding a dental model;
    whereby teeth of the dental model are received in said cavity of said tray section.

15. A protective carrier as in claim 14, wherein said carrier has an integral one piece construction, first hinge means pivotally connecting said retaining sheet to one side of said tray section, and second hinge means pivotally connecting said cover member to an opposing side of said tray section.

16. A protective carrier for a dental model used in producing a dental prosthesis, said carrier comprising:
    three interleaved sections;
    a first of said sections including a tray section provided with a recessed cavity for receiving a pedestal portion of a dental model;
    a second of said sections including a retaining sheet disposable onto said tray section, said retaining sheet including engagement means for holding the dental model in said cavity;
    a third of said sections including a cover member for closing onto said retaining sheet to protectively secure the dental model in said carrier when said carrier is in a closed position with said retaining sheet disposed between said tray section and said cover member;
    said cover member including a recessed chamber for overlying the dental model retained in said cavity;
    a plurality of radially extending stiffening ribs being provided along a base of said chamber; and
    a circular stiffening boss projecting from said base of said chamber, said stiffening ribs radially extending from said boss.

17. A protective carrier as in claim 16, wherein said carrier has an integral one piece construction, first hinge means pivotally connecting said retaining sheet to one side of said tray section, and second hinge means pivotally connecting said cover member to an opposing side of said tray section.

18. A protective carrier for a dental model used in producing a dental prosthesis, said carrier comprising:
    three interleaved sections;
    a first of said sections including a tray section provided with a recessed cavity for receiving a pedestal portion of a dental model;
    a second of said sections including a retaining sheet disposable onto said tray section, said retaining sheet including engagement means for holding the dental model in said cavity;
    a third of said sections including a cover member for closing onto said retaining sheet to protectively secure the dental model in said carrier when said carrier is in a closed position with said retaining sheet disposed between said tray section and said cover member;
    said cover member including a recessed chamber for overlying the dental model retained in said cavity;
    said recessed chamber including a peripheral wall; and
    a plurality of grooves being provided in said peripheral wall.

19. A protective carrier as in claim 18, wherein said carrier has an integral one piece construction, first hinge means pivotally connecting said retaining sheet to one side of said tray section, and second hinge means pivotally connecting said cover member to an opposing side of said tray section.

20. A protective carrier for a dental model used in producing a dental prosthesis, said carrier comprising:
    three interleaved sections;
    a first of said sections including a tray section provided with a recessed cavity for receiving a pedestal portion of a dental model;
    a second of said sections including a retaining sheet disposable onto said tray section, said retaining sheet including engagement means for holding the dental model in said cavity;
    a third of said sections including a cover member for closing onto said retaining sheet to protectively secure the dental model in said carrier when said carrier is in a closed position with said retaining sheet disposed between said tray section and said cover member; and
    said retaining sheet being corrugated for improved stiffness.

21. A protective carrier as in claim 20, wherein a smooth border is provided about a periphery of said retaining sheet.

22. A protective carrier as in claim 20, wherein said carrier has an integral one piece construction, first hinge means pivotally connecting said retaining sheet to one side of said tray section, and second hinge means pivotally connecting said cover member to an opposing side of said tray section.

* * * * *